United States Patent
Berry et al.

[11] Patent Number: 5,240,854
[45] Date of Patent: Aug. 31, 1993

[54] CONTINUOUS HIGH-DENSITY CELL CULTURE SYSTEM

[76] Inventors: Eric S. Berry, 32 Valleyview Dr., Merrimack, N.H. 03054; Mark J. Ramberg, 24 Brattle St., Worcester, Mass. 01606

[21] Appl. No.: 708,823

[22] Filed: May 28, 1991

Related U.S. Application Data

[63] Continuation of Ser. No. 361,141, Jun. 5, 1989, abandoned.

[51] Int. Cl.⁵ .............................................. C12M 3/00
[52] U.S. Cl. ................................ 435/284; 435/300; 435/301; 435/310
[58] Field of Search .............. 435/289, 300, 301, 310, 435/284, 285

[56] References Cited

U.S. PATENT DOCUMENTS

| | | | |
|---|---|---|---|
| 3,407,120 | 10/1968 | Weiss et al. | 195/104 |
| 3,734,851 | 5/1973 | Matsumura | 210/22 |
| 3,827,943 | 8/1974 | Mann | 435/289 |
| 3,843,454 | 10/1974 | Weiss | 195/127 |
| 3,853,712 | 12/1974 | House et al. | |
| 3,948,732 | 4/1976 | Haddad et al. | 195/127 |
| 4,172,013 | 10/1979 | Skoda et al. | 435/240 |
| 4,225,671 | 9/1980 | Puchinger et al. | 435/71 |
| 4,228,243 | 10/1980 | Iizuka | 435/285 |
| 4,307,193 | 12/1981 | Iizuka | |
| 4,377,639 | 3/1983 | Lee | 435/285 |
| 4,654,308 | 3/1987 | Safi et al. | 435/310 |
| 4,661,455 | 4/1987 | Hubbard | 435/240 |
| 4,661,458 | 4/1987 | Berry et al. | 261/104 |
| 4,720,462 | 1/1988 | Rosenson | 435/289 |
| 4,734,373 | 3/1988 | Bartal | 435/301 |

FOREIGN PATENT DOCUMENTS 0121981 10/1984 European Pat. Off. .
0205790 12/1986 European Pat. Off. .

Primary Examiner—Carroll B. Dority
Attorney, Agent, or Firm—Wolf, Greenfield & Sacks

[57] ABSTRACT

A multi-chamber cell-culture assembly has provision for even and continuous distribution of nutrient medium throughout each of the chambers. A device is constructed to provide large surface areas for cell growth relative to the chamber volumes. Cell growth, nutrient addition and cell product withdrawal may be carried out automatically.

16 Claims, 5 Drawing Sheets

CONTINUOUS HIGH-DENSITY CELL CULTURE SYSTEM

This application is a continuation of application Ser. No. 07/361,141, filed Jun. 5, 1989 and now abandoned.

This invention relates to a method and apparatus for the culture of cells.

Conventionally, cells have been grown attached to glass or plastic roller bottles and flasks. This approach does not lend itself to high-density growth of cells or continuous cell culture, and requires large amounts of medium and space. Further, this approach is labor intensive.

To achieve higher-density growth conditions, various attempts have been made to use arrangements of stacked plates, the surfaces of the stacked plates providing increased surface area for cell attachment and growth. In spite of the various attempts, the cell-culturing devices of the prior art all have various drawbacks, including the need for excessive amounts of medium, the inability to provide a continuous flow of nutrients to all cell-growth surfaces, the need for labor-intensive monitoring and care of the growing cells and the inability to operate continuously.

SUMMARY OF THE INVENTION

An object of the invention is to provide a cell culture device in which cells may be grown to a high density relative to the amount of nutrient medium contained within the system.

Another object of the invention is to provide a cell culture assembly having a plurality of growth chambers receiving medium flow equally.

Another object of the invention is to provide a cell culture assembly that allows for the automatic, continuous addition of nutrient medium and the removal of conditioned medium containing the products and waste formed by the cells.

Another object of the invention is to provide a cell culture assembly and system in which the cellular environmental condition is continuously monitored, with any departures from the desired conditions being automatically corrected or alarmed.

Another object of the invention is to provide a continuous flow system to facilitate a desirable chemostatic environment for the cells and to facilitate optimal yield and harvesting ability for cell products such as biochemicals, vaccine virus, and pharmaceuticals.

The invention provides a continuous cell culturing device having an array of growth chambers defining a very large surface area for high-density cell growth in a small volume. The device is constructed and arranged to permit directional flow through the growth chambers, the flow being continuous and capable of reaching all growth surfaces within each chamber. Adequate flow in each chamber is accomplished by providing each chamber with a fluid restriction port, these ports acting to control the flow and distribution of fluid into each of the growth chambers.

Preferably, the cell culturing device includes an array of cell growth chambers defined by the spaces between a plurality of stacked plates An inlet conduit provides a source of nutrient medium to a manifold in fluid communication with the cell growth chambers via the fluid restriction ports. The sum of the cross-sectional areas of the narrowest region of the fluid restriction ports is less than the cross-sectional area of the inlet conduit, thereby ensuring a pressure drop across each of the fluid restriction ports and adequate flow of fluid through each growth chamber.

Preferably, the fluid restriction ports and growth chambers are constructed and arranged to promote the distribution and continuous directional flow of fluid medium to all growth surfaces with a minimum of turbulence. This may be accomplished by providing growth chambers that are essentially square boxes, with an inlet restriction port and an outlet restriction port at opposing corners of the box. The fluid restriction ports may have a constricted intermediate section, and the corners may have curved surfaces to promote fluid distribution and nonturbulent flow. Ribs may be provided between opposing faces of the plates to provide structural support and further to direct fluid flow.

The invention thus provides a closed sterile system for the culture of cells and prevents both exposure of personnel to the cells and their products and the contamination of the culture from the outside environment. Growth conditions may be sensed automatically, with nutrients added and cell-products removed responsive to the sensed condition. The device can be supplied economically and can be manufactured in large scale production.

DETAILED DESCRIPTION OF THE DRAWINGS

Figure 1:
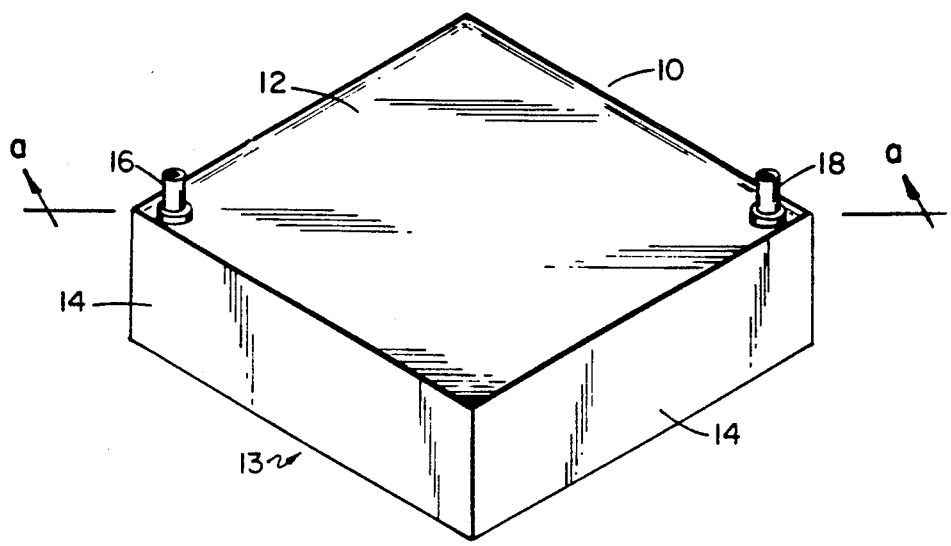
FIG. 1 is a perspective view from the top right of the cell culture vessel of the invention.

The cell culture device of the preferred embodiment includes an array of growth chambers enclosed within a vessel. The growth chambers provide a large surface area for cell growth. In exterior view (FIG. 1), the vessel 10 is a substantially square box with square, molded top 12 and base 13, and vertical molded sidewalls 14 sealed along the edges to provide a fluid-tight arrangement for housing the growth chambers. Extending from diagonally opposed corners of the top 12, are an inlet conduit 16 and an outlet conduit 18. The inlet conduit 16 provides fluid access to the interior space of the vessel 10, and the outlet conduit 18 provides fluid egress from the interior space of the vessel 10. The outlet conduit 18 may extend through the base 13, rather than through the top 12 as shown.

Figure 2:
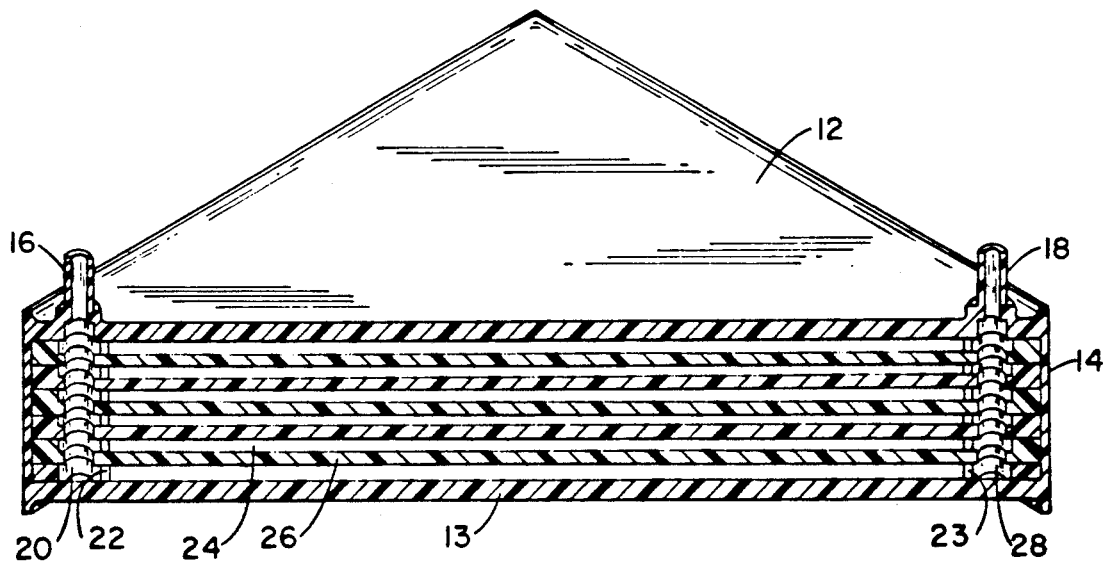
FIG. 2 is a perspective cross-sectional view taken along line a—a of FIG. 1.

Referring to FIG. 2, the inlet conduit 16 is in axial alignment and in fluid communication with an inlet manifold 20 extending transversely through the interior space of the vessel 10 at the corner. Inlet restriction ports 22 provide fluid communication between the manifold 20 and a plurality of cell growth chambers 24 located within vessel 10, which chambers 24 are defined on upper and lower extents by an array of stacked plates 26. At the corner of the vessel opposite the inlet manifold 20 is an outlet manifold 28 in fluid communication with the outlet conduit 18. Each growth chamber 24 is in fluid communication with the outlet manifold 28 via an outlet fluid restriction port 23. The inlet and outlet manifold arrangements in the preferred embodiment are mirror images of one another and, therefore, the flow characteristics will be the same whether the fluid medium is flowing from the inlet and to the outlet ends or vice versa.

The relative size of the restriction ports 22,23 and conduits 16,18 form an important part of the invention. To ensure that each chamber receives a continuous and controlled flow of fluid medium, a pressure drop must be created across the flow restriction port controlling flow within each chamber. To achieve this, the sizes of the restriction ports controlling flow are selected such that the sum of the cross-sectional areas of the narrowest portion of these restriction ports is equal to or preferably less than the cross-sectional area of the inlet conduit. Preferably, the sum of these cross-sectional areas also is equal to or less than the cross-sectional area of the outlet conduit. When these conditions are present, no particular growth chamber will be favored due to its location, and all growth chambers will receive fluid medium based principally upon the particular size of the fluid restriction port controlling flow in that chamber. Preferably, the fluid restriction ports are uniformly dimensioned so that each growth chamber will receive fluid medium at an identical flow rate.

In the embodiment shown, there are flow restriction ports at both the inlet and the outlet end of the growth chambers. The smaller of the inlet and outlet restriction ports will control the flow through a particular growth chamber, without regard to its location at the inlet or outlet end. Thus, it is the sum of the cross-sectional areas of the smaller of the inlet and outlet restriction ports for each chamber that should be less than the cross-sectional area of the conduits. If a pair of inlet and outlet restriction ports are uniformly dimensioned and have the same cross-sectional area at their narrowest portion, then in calculating the sum of the cross-sectional areas as described above, only one cross-sectional area is included.

The plates 26 are stacked to form the growth chambers. Preferably, the plates are spaced 1 mm apart or greater. Although the plates may be spaced closer to one another, air bubbles tend to become trapped between the plates and interrupt the even flow of medium when spaced less than 1 mm apart. The surfaces of the plates may be roughened, corrugated, convoluted or otherwise irregular to increase their surface area and the number of cells capable of growing on a given plate. If irregular, the 1 mm spacing between the plates should be between the facing peaks of irregular surfaces. The surfaces of the plates also may be surface treated in a variety of different ways to promote cell growth. Typical treatments include carboxyl group treatments, collagen treatments, fibronectin treatments or feeder cell layers.

The plates according to the preferred embodiment were molded from K-resin, a block co-polymer of polystyrene and butadiene, sold by Phillips Chemical Co., Bartlesville, Okla., 74004. Suitable plate materials include styrenic materials or materials such as polymethyl pentene. However, the plate may be of virtually any material that is sufficiently strong, nontoxic, biocompatible, and otherwise suitable for tissue culture.

Figure 3:
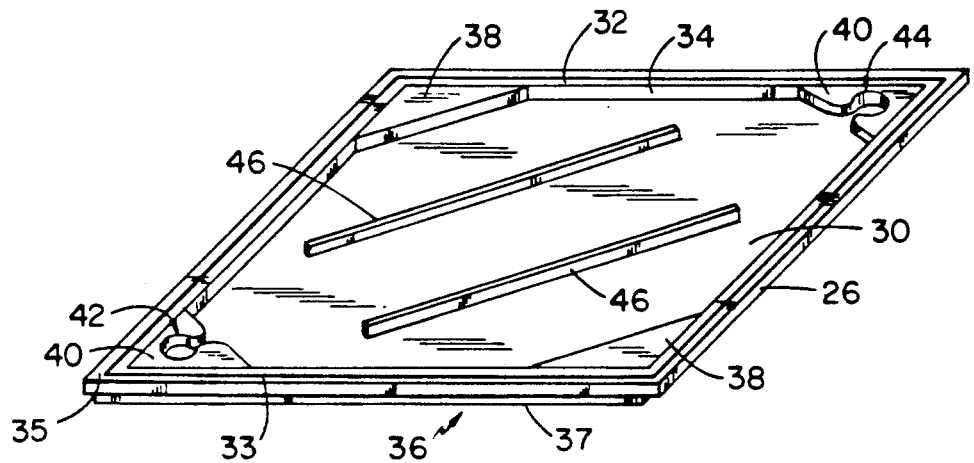
FIG. 3 is a perspective view from the top front of a single culture plate used in forming the cell culture vessel of FIG. 1.
Figure 4:
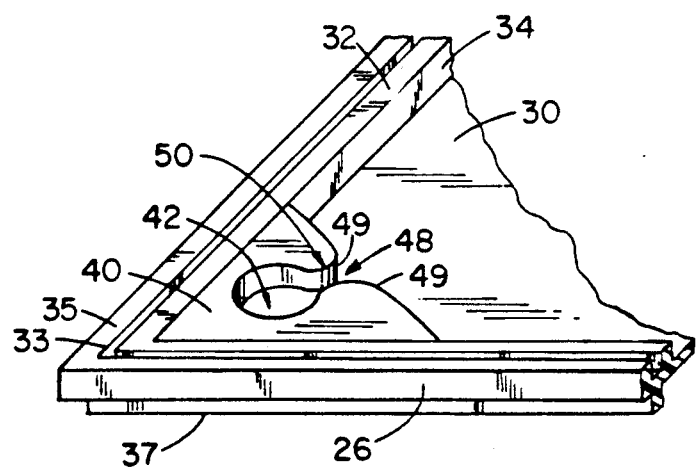
FIG. 4 is an enlarged view of a corner of the plate of FIG. 3.

The plates of the preferred embodiment have a novel construction which facilitates flow distribution and manufacture. Each plate 26 has an upper surface 30 bounded by a peripheral wall 32 (FIG. 3). The inside facing surface 34 of wall 32 along with the plate upper surface 30 define the side walls and floor of a growth chamber 24. When the plates 26 are stacked in the assembled device, the top edge 35 of wall 32 mates and seals with the lower surface 36 of the adjacent plate to define a growth chamber, the ceiling of the chamber being defined by the lower surface 36 of the adjacent plate. To facilitate the mating arrangement of the stacked plates, the wall 32 is provided on its top edge 35 with a groove 33 for receiving a mating ridge 37 on the bottom surface of an adjacent plate. The mating ridge 37 and groove 33 align the stacked plates.

The four corners 38,40 of each plate 26 are solidly filled-in to a thickness equal to the height of the peripheral wall 32. The filled corners add support to the assembled structure. The filled corners further reduce the potential for fluid turbulence and "dead spots," as will be explained more fully below.

Each plate 26 has a bore at diagonally-opposed, filled corners 40. In the assembled condition, the bores 42,44 of the stacked plates 26 are axially aligned and form the inlet and outlet manifolds 20,28, respectively. A passage 48 extends from each bore 42,44 through the filled corners 40 to the interior space defined by the side walls and floor of each plate 26. These passages in the assembled condition form the fluid restriction ports 22, 23 providing fluid access between the manifolds 20,28 and the growth chambers 24. Each passage has a floor defined by a portion of the upper surface 30 of the plate 26 and sidewalls 49 formed integrally as part of the corners 40 and having a height equal to the peripheral ridge 32. The fluid restriction ports 22, 23 are formed when the flat bottom surface of an opposing plate 26 is stacked to seal the open upper extremity of the passage 48.

The particular shape of the fluid restriction port in the preferred embodiment includes a narrowed internal portion, as at constriction 50. The diameter of the flow restriction port 22 then increases continuously and substantially in a direction toward the growth chamber 24. This arrangement causes medium entering the growth chamber to flare out and be evenly dispersed in a radial pattern into the growth chamber space, promoting nutrient supply and even fluid flow across the entire growth surface. This arrangement also reduces turbulence, especially at and around the restriction ports 22. In the embodiment shown, the diameter of the flow restriction port increases linearly. However, a port shaped as a second or third order venturi would provide for continuous, gradual change in velocity, thereby further promoting nonturbulent flow.

The nonturbulent and directional flow pattern is further facilitated by the filled corners 38 and by flow-guiding ribs 46 The corners, if not filled, would provide a wall perpendicular to the direction of flow which in turn would result in turbulence and "dead spots," areas within the growth chamber not receiving a continuous and directional flow of fresh media resulting in cell death. The filled corners provide a curved surface which acts to channel flow continuously in the direction of the outlet ports. The ribs 46 provide a dual function. They serve to provide structural support to each plate maintaining the plates ar the proper spacing, even when draining the device under a vacuum, and also may be positioned to channel flow continuously in a direction toward the outlet ports.

To assemble the device, the plates must be stacked and secured to one another in a manner to seal the peripheral walls and corners of the plates to the bottom surfaces of opposing plates. Presently, each plate is welded to an adjacent plate by ultrasonic welding However, any method of fabrication such as solvent welding, RF welding, potting, glue or even gaskets would be acceptable, so long as the final product has sufficient strength and is nontoxic to cultured cells.

In operation, the device first is seeded with cells. Then, fluid media is supplied to the attached cells as follows. Fluid medium is introduced into inlet manifold 20 via inlet conduit 16. The fluid medium then passes through the various flow restriction ports 22 into the associated growth chambers 24. Because of the overall construction of the flow restriction ports and the growth chambers, flow is distributed continuously and thoroughly to all surfaces of the growth chamber 24, the fluid medium always moving generally in a direction toward the outlet flow restrictors 23. The medium then passes through the outlet flow restrictors 23, into the outlet manifold 28 and then our of the device via the outlet conduit 18.

Figure 5:
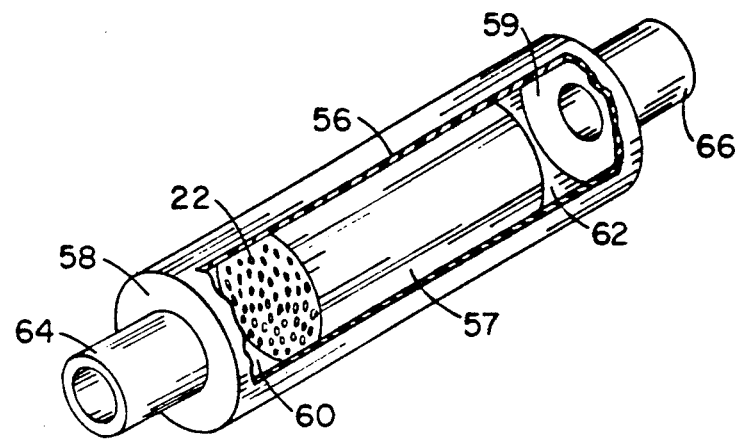
FIG. 5 is a perspective view of a cylindrical embodiment of a cell culture vessel of the invention, with the near side of the device casing removed to show the surface and end of the enclosed growth chamber.

Another embodiment cf the device comprises a cylindrical casing containing an array of longitudinally oriented culture chambers. As shown in FIG. 5, a cylindrical casing 56 encloses and is sealed to the outside surface of a cylindrical culture chamber 57. The casing 56 is sealed at each end with two circular end plates, inlet end plate 58 and outlet end plate 59, each of which is spaced slightly from the opposite ends of the culture chamber 57. The spacing between the inlet end plate 58 and the inlet end of the culture chamber 57 defines an inlet manifold 60. The spacing between the outlet end plate 59 and the outlet end of the culture chamber 57 defines an outlet manifold 62 Fluid enters the inlet manifold 60 via an inlet conduit 64 which is fluidly attached to and extends axially from inlet end plate 58. Fluid exits the outlet manifold 62 via an outlet conduit 66 which is fluidly attached to and extends axially from outlet end plate 59.

Figure 6:
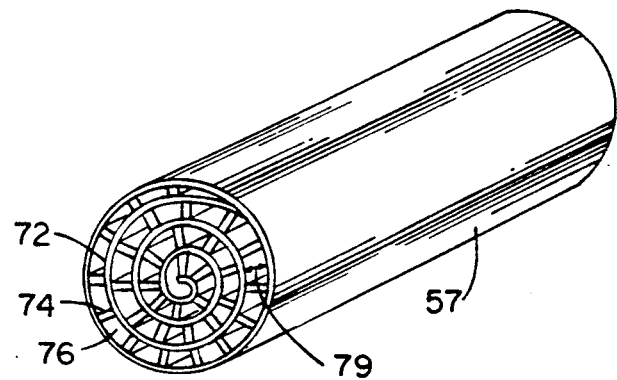
FIG. 6 is an end view in cross-section of the spiralled growth chamber of FIG. 5.

The longitudinally extending growth channels of the culture chamber 57 are formed by rolling a rectangular, flexible sheet 72 formed with a plurality of longitudinally-oriented, projecting ridges 74. Upon rolling the sheet from a side parallel to the projecting ridges 74, the sheet 72 assumes the shape of a spiral cylinder (FIG. 6). The projecting ridges 74 along with the overlapping turns of the rolled sheet 72 define a longitudinal array of channels 76, the height of the ridges 79 defining the height of each channel 76. The open ends of the channels 76 are plugged or capped to provide restriction ports 22, limiting fluid access to each channel 76.

The operation of this embodiment is similar to that described above. First the device is seeded with cells which are allowed to attach to the surfaces of the channels 76. Then, fluid medium is introduced via the inlet conduit 64 into inlet manifold 60. Fluid medium then passes from the manifold into the longitudinally extending growth chambers 76 via the inlet restriction ports 22. The fluid medium passes continuously along the length of the growth channel 76, passes through the outlet restriction ports (not shown) and exits the device via the outlet manifold 62 and outlet conduit 66.

Figure 7:
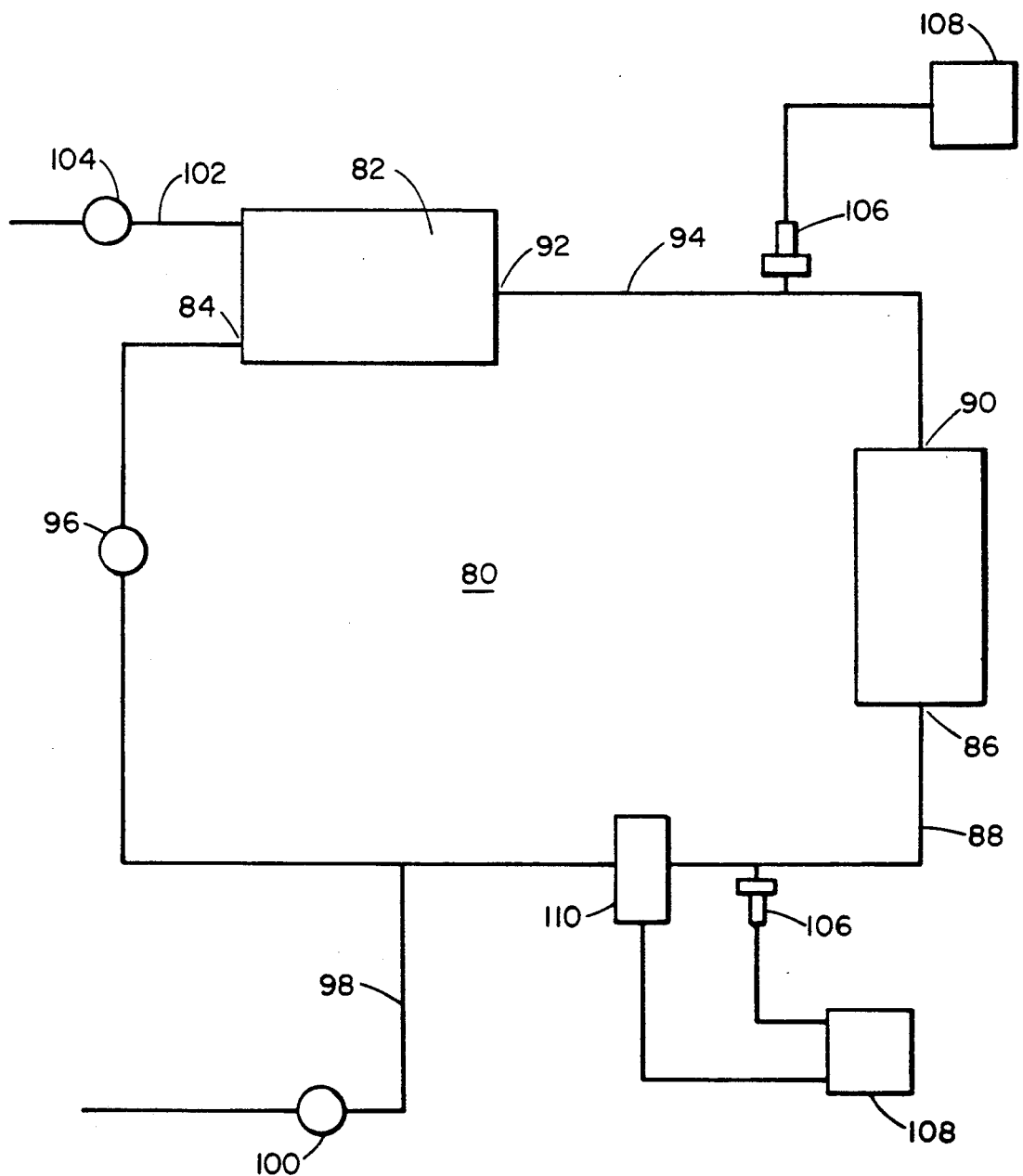
FIG. 7 is a schematic view of a cell culture vessel of the invention in a continuous cell culture assembly.

According to one aspect of the invention, the cell culture device of the invention is provided as part of an assembly 80 as depicted schematically in FIG. 7. The assembly 80 is constructed and arranged for continuous operation. The assembly 80 is a closed-loop system connecting the culture vessel 10 of the invention with a fluid reservoir 82. An outlet port 84 of the reservoir 82 is connected to the inlet port 86 of the culture vessel 10 via a fluid supply conduit 88 The outlet end 90 of the culture vessel 10 is in fluid communication with an inlet port 92 of the reservoir 82 via fluid return conduit 94. A pump 96 is positioned along the fluid supply conduit 88 for continuously pumping fluid medium from the reservoir through the culture vessel 10. A nutrient supply line 98 is fluidly connected to the fluid supply conduit 88 between pump 96 and vessel 10 such that nutrients may be added to the fluid supply conduit 88. A pump 100 is provided for pumping the nutrients into the fluid supply conduit 88. The reservoir 82 also is provided with a product withdrawal conduit 102 connected to a withdrawal pump 104 for removing fluid downstream of the culture vessel, preferably continuously. Finally, the assembly is provided with probes 106 on the fluid supply conduit 88 and the fluid withdrawal conduit 94. These probes 106 provide means for sensing the condition of the medium These probes may be connected to a control device 108 which in turn is connected to the various pumps for controlling the introduction of nutrients and withdrawal of products from the reservoir based upon the condition of the medium. Optionally, oxygen exchange means 110 may be provided for continuous resupply of oxygen to the culture medium. Preferably, the nutrient supply pump 100 and the product withdrawal pump 104 are operated continuously and at the same rate such that resupply medium is continually being introduced and product is continually withdrawn from the system, the rate of pumping being determined by the control means.

As discussed above, it is not necessary that the flow restriction ports be of a uniform size If uniform flow through each chamber is desired, then, generally speaking, it is necessary that the flow restriction ports be of the same dimensions. However, it will be understood by one of ordinary skill in the art that flow will depend not only upon the size of the flow restriction port, but also on the particular dimensions cf the growth chamber. Thus, the relative size of the flow restriction port and growth chamber together may be varied while maintaining a particular flow rate.

In the preferred embodiment, only one pair of restriction port per growth chamber has been described. It is, of course, possible to have many flow restrictors on the inlet or the outlet side. The inventors currently prefer one inlet and outlet restriction port as it facilitates manufacture, it lessens turbulence, and reduces the lack of cell growth normally found at and very close to the flow restriction ports.

It further will be understood by one of ordinary skill in the art that it is possible to have flow restriction ports on the inlet side only. A vessel of such construction may be preferred for applications requiring the recovery of cells from the vessel, as conventional methods for removing cells from culture vessels tend to yield cell clumps which may clog a constricted outlet. It also is possible to have restriction ports on the outlet side only.

However, having flow restriction ports on the inlet and outlet side presently is preferred.

It further is preferred that the sum of the cross-sectional areas of the flow restriction ports be less than or equal to the cross-sectional area of the outlet conduit. Otherwise the outlet conduit will set up a back-pressure which may result in preferential flow through one or more growth chambers.

Figure 8:
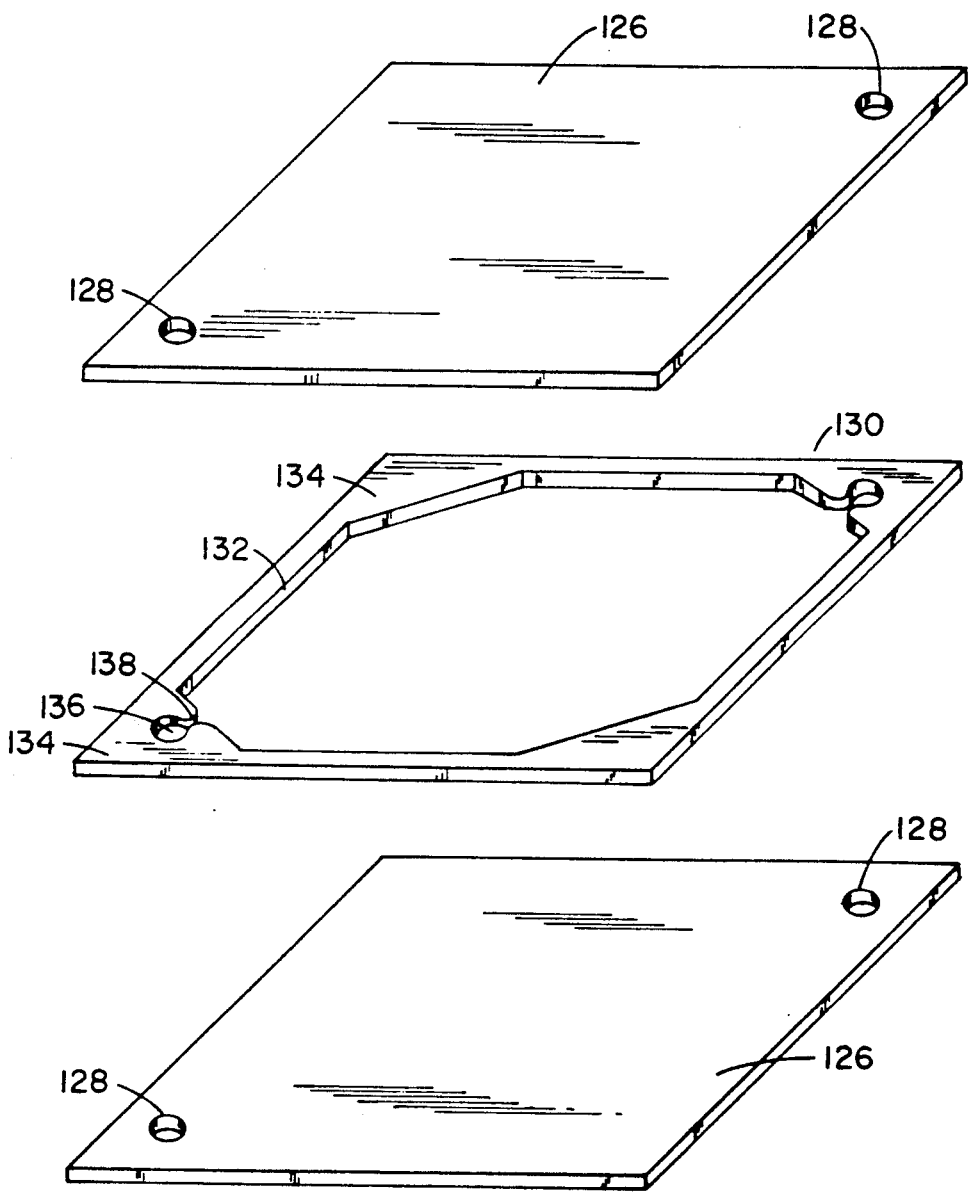
FIG. 8 is an exploded front view of one embodiment of a plate assembly, with a gasket defining the height and configuration of the space between plates used in forming the culture vessel of FIG. 1.

In another embodiment, a cell culture vessel similar to that depicted in FIGS. 1-4 may be formed of a series of flat plates sandwiching gaskets, the gaskets forming the side walls and restriction ports of the growth chambers (FIG. 8). In this embodiment, the plates 126 have substantially flat upper and lower surfaces. A transverse bore 128 is located at each of a pair of opposing corners of each plate. The gasket 130 has a perimeter corresponding in size and shape to the perimeter of the plates 126. The interior facing walls 132 of the gasket 130 define a hollow space. When a pair of plates 126 sandwiches a gasket 130, the facing surfaces of the plates 126 form the upper and lower extents of a growth chamber, while the interior facing walls 132 of the gasket form the side walls of the growth chamber.

The corners 134 of the gasket are filled. A pair of opposing corners each has a gasket bore 136 extending therethrough, these gasket bores 136 corresponding in size and shape to the bores 128 at opposing corners of the plates 126. A passage 138 extends from the gasket bore 136 inwardly through the corner to the interior space defined by the inwardly facing walls 132 of the gasket 130. The bore and the passage essentially define an indentation in the interior facing gasket wall 132 as can be clearly seen in FIG. 8. When a pair of plates 126 sandwiches a gasket 130, the bores 128 of the plates 126 and the gasket bores 136 align to form manifolds. The passage 138 is closed off on upper and lower extents by the stacked plates to form the restriction ports.

An assembly of such stacked plates and gaskets may be held together by a compressive force, such as by clamps. This particular embodiment of the invention has as an advantage the ability to separate the plates from one another after cells have been grown. This allows a monolayer of cells or "skin" to be peeled from the surface of the plates and otherwise facilitates access to the cells on the surface of a plate.

The cell culture assembly used in this example was constructed substantially as shown in FIG. 7 (excluding the probes and oxygen exchange means).

The cell culture vessel used in the assembly had the following characteristics. Ten plates were stacked and secured to one another by ultrasonic welding. The bottom plate formed the bottom of the vessel. A top plate having both inlet and outlet conduit attachment sites was sealed to the upper most plate to form the upper most growth chamber. The top plate was clamped in place and secured by potting all four sides of the stacked arrangement. Each plate was approximately 1.5 mm in thickness and each plate included an approximately 1 mm high wall with filled corners. When stacked, the plates formed growth chambers approximately 1 mm in height and 22 mm in length and width. The restriction ports at their narrowest portion, were approximately 1 mm in height by 2 mm in width, defining a cross-sectional area of about 2 $mm^2$. The cylindrical inlet conduit was approximately 5 mm in diameter, defining a cross-sectional area of about 49 $mm^2$. Thus, the cross sectional area of the inlet conduit (49 $mm^2$) was greater than the sum of the cross-sectional areas of the narrowest portions of the restriction ports (20 $mm^2$).

The cells used in this example were VERO cells, obtained from the American Type Culture Collection, Rockville, Md. under ATCC number CCL-81. VERO cells were grown in a roller bottle (900 $cm^2$, CoStar Corporation, Cambridge, Mass. ) to a density of $5.0 \times 10^8$ cells. The cells then were aseptically trypsinized to release the cells from the bottle surface, and then the cells were resuspended in 15 ml of MEM (Gibco, Grand Island, N.Y.) plus 5 ml of FBS (Fetal Bovine Serum, Sigma, St. Louis, Miss.).

The assembly was filled with 1250 ml fluid medium (MEM in 5% FBS), and then the vessel was loaded with cells on day 0 by injecting the cells through a sterile septum, located in the fluid supply conduit, while fluid medium was being advanced into the vessel by a pump. Loading was carried out while the vessel was in its normal operation position, (standing on its side in a vertical position with the inlet conduit on the bottom and the outlet conduit on the top). In this position, any bubbles entering the vessel rise and exit the vessel. The pump was operated continuously while the cells were injected slowly into the fluid medium stream, the pump and injection of cells being stopped at a time determined to be approximately 90% of the time required to move media from the injection site to the outlet port of the vessel. This method of loading the cells provided a constant dilution on injection and a uniform disposal of cells across all the growth chambers of the vessel. The vessel then was placed on its bottom surface for four hours to allow the cells to attach to that surface. The loading procedure then was repeated except that the vessel was placed in a horizontal position on its top surface to allow cells to attach to that surface.

After the vessel was seeded with cells and the cells were allowed to attach, the pump 88 was started and operated continuously at a rate of 75 ml per minute throughout the first 24 hours. Beginning at day 2 and over the course of the next 24 hours, additional fluid medium was added to the system to bring the total volume to 1,750 ml. Further on day 2, the pump rate was increased from 75 ml per minute to 150 ml per minute. Then on day 3, the pump was increased to a rate of 300 ml per minute and operated at that rate continuously through day 5. During the 5 days of operating the pump, 5% $CO_2$ was circulated over the surface of the fluid medium within the reservoir. (Approximately 25 ml per minute). After 5 days of growth, the vessel was disconnected from the assembly and flushed with saline. This was followed by introducing gluteraldehyde (in saline) into the vessel to fix the cells. The cells then were stained with Wright stain. After staining, the vessel was cut open so that the stained cells could be inspected. The surfaces of the plates were completely covered with a uniform layer of cells.

During the 5 day growth period, the quantity of glucose consumption was monitored. Glucose was consumed as follows:

| Day | Mg/Day |
|---|---|
| 1 | 320 |
| 2 | 1,015 |
| 3 | 1,800 |
| 4 | 2,100 |
| 5 | 2,270 |

Throughout the 5-day growth period, fresh medium was introduced through the nutrient supply conduit at an increasing rate corresponding to the change in glucose consumption. A corresponding amount of used medium was removed via an overflow conduit in the reservoir. Because the system had a capacity of 1750 ml, any increase beyond that amount resulted in an overflow. Therefore, once the system was completely filled, the addition of any new fluid medium caused a corresponding removal of an equal amount of used medium from the fluid reservoir.

Glucose was monitored by inserting a syringe into the septum and removing a small sample of fluid medium. The glucose level of this sample then was tested at a site remote from the cell culture assembly. However, as described in the in specification, the assembly could be provided with on line probes for monitoring glucose and the like continuously.

It should be understood that various changes and modifications of the embodiments described may be made within the scope of the invention. It is intended that all matte contained in the above description or shown in the accompanying drawings shall be interpreted in an illustration and not limiting sense.

What I claim is:

1. A tissue culture device comprising:
   a plurality of cell growth cambers, the interior surfaces of the chambers adapted for the growth of cells;
   an inlet conduit for providing a source of fluid to the chambers;
   an outlet conduit for channeling fluid from the chambers; and fluid restriction means for providing fluid communication between at least one of the conduits and each of the growth chambers, wherein the sum of the cross-sectional areas of the narrowest portion of the fluid restriction means is equal to or less than the cross-sectional area of the narrowest portion of the inlet conduit, thereby insuring a pressure drop across each of the fluid restriction ports and an adequate flow of fluid through each growth chamber.

2. A tissue culture device as claimed in claim 1 wherein the cell growth chambers are defined by the spacings between a plurality of stacked plates.

3. A tissue culture device as claimed in claim 2 wherein said fluid restriction ports and said plates are constructed and arranged to provide for the nonturbulent flow of fluid continuously and directionally from an inlet end of said chambers to an outlet end.

4. A tissue culture device as claimed in claim 2 wherein the plates are spaced at least 1 mm apart.

5. A tissue culture device as claimed in claim 2 wherein the plates are substantially square and wherein said fluid restriction means comprises fluid restriction ports at a pair of opposing corners of the plates.

6. A tissue culture device as claimed in claim 2 further comprising support ribs separating the plates.

7. A tissue culture plate which may be stacked with similar plates to form a plurality of tissue culture chambers, the plate comprising,
   a molded rectangular platform, the platform having a substantially flat upper and lower surface, at least one of the surfaces having a peripheral ridge and the plate further including a pair of diagonally opposing corners, the corners being filled to the height of the peripheral ridge,
   a bore through each of said filled corners, the bore having an axis perpendicular to the plane defined by the platform, and
   a second passage communicating between the bore and the interior space defined by the ridges and platform.

8. A tissue culture plate as claimed in claim 7 wherein said plate further includes a support rib integral with the upper surface of the plate.

9. In a tissue culture device having a plurality of growth chambers and inlet ports providing fluid access to the growth chambers, the improvement comprising inlet ports having a narrowed, intermediate section and an increasing diameter in a direction toward the growth chamber whereby fluid passing through the inlet port into the growth chamber is dispersed in a wide-angle, radial pattern.

10. A tissue culture device as claimed in claim 2 wherein said cell growth chambers are defined by the spacings between a plurality of stacked plates separated by gaskets.

11. A tissue culture device as claimed in claim 10 wherein the gaskets and plates form a stacked array and wherein the tissue culture device is constructed and arranged whereby the plates may be separated from the stacked array.

12. A tissue culture device as claimed in claim 10 further comprising means for releasibly securing the plates and gaskets in stacked array.

13. A tissue culture device as claimed in claim 1 or 2 further comprising,
   an inlet manifold located between said inlet conduit and said plurality of cell growth chambers, and wherein said fluid restriction means is located between said inlet manifold and each of said cell growth chambers.

14. A tissue culture device as claimed in claim 13 wherein said fluid restriction means and said plates are constructed and arranged to provide for the nonturbulent flow of fluid continuously and directionally from an inlet end of said chambers to an outlet end.

15. A tissue culture device as claimed in claim 13 wherein said fluid restriction means has a narrowed, intermediate section and an increasing diameter in a direction toward each growth chamber, whereby fluid passing through the inlet port into the growth chamber is dispersed in a wide-angle, radial pattern.

16. A tissue culture device as claimed in any one of claims 1, 13, 14 or 15 further comprising an outlet manifold located between said outlet conduit and said cell growth chambers, and wherein said restriction means is located between said outlet manifold and said growth chambers.

* * * * *